United States Patent [19]

Dai

[11] 4,334,106

[45] Jun. 8, 1982

[54] PROCESS FOR THE PREPARATION OF HYDROXYPHENYL-INDANOLS

[75] Inventor: Shenghong A. Dai, Wallingford, Conn.

[73] Assignee: The Upjohn Company, Kalamazoo, Mich.

[21] Appl. No.: 231,789

[22] Filed: Feb. 5, 1981

[51] Int. Cl.³ .................. C07C 37/11; C07C 37/20; C07C 39/12
[52] U.S. Cl. ........................... 568/719; 568/721; 568/727; 568/732; 568/734; 568/736
[58] Field of Search .............. 568/719, 721, 743, 732, 568/734, 736, 727

[56] References Cited

U.S. PATENT DOCUMENTS

| | | | |
|---|---|---|---|
| 2,754,285 | 7/1956 | Petropoulos | 260/47 |
| 2,819,249 | 1/1958 | Petropoulos et al. | 260/45.95 |
| 2,979,534 | 4/1961 | Petropoulos et al. | 260/619 |
| 3,264,357 | 8/1966 | Webb et al. | 260/619 |
| 3,264,358 | 8/1966 | Webb et al. | 260/619 |
| 3,271,463 | 9/1966 | Howard | 260/619 |
| 3,288,864 | 11/1966 | Farnham | 260/619 |
| 4,260,831 | 4/1981 | Matsuhimi et al. | 568/719 |

OTHER PUBLICATIONS

Kamagami, "Chemical Abstracts", vol. 89, p. 146656c, (1978).

*Primary Examiner*—Werren B. Lone
*Attorney, Agent, or Firm*—James S. Rose; Denis A. Firth

[57] ABSTRACT

An improved process is provided for the preparation of a certain class of hydroxyphenyl-indanol compounds by the cyclization of a phenol selected from the group consisting of an isopropenylphenol, oligomers thereof, and mixtures of any of said group in any combination and proportion, by dissolving said phenol in a stoichiometric excess of an organic acid selected from the group consisting of trifluoroacetic acid, trichloroacetic acid, difluoroacetic acid, dichloroacetic acid, fluoroacetic acid, chloroacetic acid, formic acid, and mixtures thereof at a temperature falling within a range of from about 0° C. to about 90° C. to form a solution; and maintaining said solution at a temperature falling within the above said range until the formation of said indanol is substantially complete.

The dihydroxy compounds produced by the present method are useful in the preparation of epoxy, alkyd, and urethane resins in particular.

13 Claims, No Drawings

PROCESS FOR THE PREPARATION OF HYDROXYPHENYL-INDANOLS

BACKGROUND OF THE INVENTION

1. Field of the Invention

This invention relates to a process for the preparation of certain indanols and is more particularly concerned with a process for the cycli-dimerization reaction of certain isopropenylphenols and derivative forms thereof to said indanols and with processes for the conversion of phenol to certain indanols which incorporate this cyclization as a step therein.

2. Description of the Prior Art

Certain dihydric indane compounds, particularly hydroxyphenyl-indanol compounds, have been known for some time along with their use in the formation of epoxide resins and as antioxidants in rubber products. U.S. Pat. Nos. 2,754,285 and 2,819,249 disclose the preparation of these compounds via the acid catalyzed dimerization of α-methylstyrenes to form indanes, followed by sulfonation of the indanes, and subsequent fusion of the sulfonated products with potassium hydroxide. The troublesome steps of ring sulfonation followed by alkali fusion were eliminated when Petropoulos et al (U.S. Pat. No. 2,979,534) discovered that the isopropenylphenol products obtained from the cracking of certain bisphenols could be dimerized at temperatures ranging from 110° C.–160° C. to provide hydroxyphenyl-indanols directly, or, alternatively, that the cracking and dimerizing reactions could be carried on simultaneously within the temperature range of 130° to 160° C. Howard (U.S. Pat. No. 3,271,463) observed the formation of a small amount of 1-(p-hydroxyphenyl)-1,3,3-trimethyl-6-indanol along with the main product of 3,3,3',3'-tetramethyl-1,1'-spiro-6-indanol when bisphenol A was contacted with aqueous sulfuric acid at 90°–150° C.

U.S. Pat. No. 3,264,357 discloses the preparation of bis-phenols via the reaction of the mixture of the two isomeric forms of the dimer of isopropenylphenol with a phenol in the presence of a strong acid catalyst including trichloroacetic acid. This disclosure reports the formation of a hydroxyphenyl-indanol when the subject reaction is carried out in the absence of the phenol consistuent at a reaction temperature of about 90° C. U.S. Pat. No. 3,264,358 reports the preparation of 1-(p-hydroxyphenyl)-1,3,3-trimethyl-6-indanol when a mixture of the two isomeric dimers of p-isopropenylphenol are treated with a strong acid catalyst. Specifically, the dimer mixture was heated under reflux with concentrated hydrochloric acid for 2 hours.

U.S. Pat. No. 3,288,864 discloses the reaction of isopropenylphenol in the presence of Friedel-Crafts catalysts to form hydroxyphenyl-indanols at elevated temperatures.

Japanese specification No. 78 68762 (Chem. Abst. 89, 1978, 146656c) discloses the cyclization of p-isopropenylphenol in aromatic hydrocarbons or halohydrocarbons containing nitro or cyano compounds above 50° C. and in the presence of alkylating catalysts, i.e. iodine, perchloric acid, aluminum chloride, etc.

I have now discovered that, by using a certain class of strong organic acids, which serve as both solvent and catalyst, isopropenylphenols and derivative forms thereof can be converted very easily into the corresponding hydroxyphenyl-indanol compounds. Surprisingly, the conversion is very rapid, much more rapid than prior art methods, and can be accomplished at temperatures as low as normal room temperature (about 20° C.) to provide the indanols in high yields and in excellent purity.

More surprisingly, the isopropenylphenol starting material need not be in the monomeric state but can be in the derivative form of the dimer, the trimer, and higher oligomer forms, yet still be converted to the dihydric indane products in accordance with the present methods and in the same high yields as when the monomeric phenol is employed.

To the best of my knowledge, there is no known prior art method which can convert the subject isopropenylphenols and their oligomeric derivative forms into the corresponding indanols in such high yields and good purity, using such mild reaction conditions and at such a rapid rate. Generally speaking, typical prior art methods (see Example 8 below which is in accordance with Example 2 of U.S. Pat. No. 3,264,358) result in much lower yields than the instant methods.

In another unexpected aspect of the present invention, I have found that the method in accordance with the present invention is particularly useful in a semicontinuous process in which phenol is condensed with a ketone to yield a bisphenol compound, the bisphenol is subjected to alkaline pyrolysis to yield a mixture of phenol and a p-isopropenylphenol compound. Distillation of the mixture to recover the regenerated phenol leaves a residue comprised of a mixture of the p-isopropenylphenol and its dimerized form as the major components. The latter mixture is subjected to the method of this invention to obtain the corresponding hydroxyphenylindanol and the regenerated phenol compound is reused in a further cycle of operations.

SUMMARY OF THE INVENTION

This invention comprises a method for preparing a hydroxyphenyl-indanol having the formula

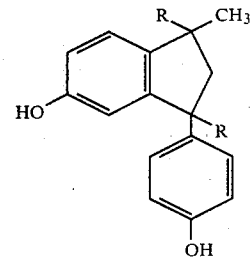

I wherein R is lower alkyl, which comprises dissolving a phenol selected from the group consisting of an isopropenylphenol having the formula:

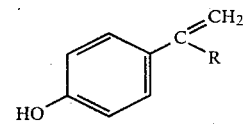

II wherein R is defined above, oligomers thereof and mixtures of any of said groups in any combination and proportion, in a stoichiometric excess of an organic acid selected from the group consisting of trifluoroacetic acid, trichloroacetic acid, difluoroacetic acid, dichloroacetic acid, fluoroacetic acid, chloroacetic acid, formic acid, and mixtures thereof at a temperature falling within a range of from about 0° C. to about 90° C. to form a solution; and maintaining said solution at a temperature falling within the above said range until the formation of said indanol is substantially complete.

The invention also comprises a semi-continuous method for the conversion of phenol to an indanol according to formula (I) which comprises condensing phenol and a ketone of the formula RCOCH₃ (III) wherein R is defined above, in the presence of acid to obtain the corresponding bisphenol of formula

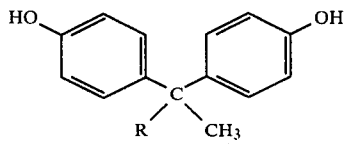

wherein R is defined above, subjecting said bisphenol to distillation in the presence of a catalytic amount of an alkali metal hydroxide to yield a mixture of phenol and the p-substituted phenol according to the formula (II), recovering the phenol by distilling it from said mixture for reuse as part of the starting material in a subsequent cycle of the above steps, treating the residue from said distillation which comprises predominantly a mixture of said p-isopropenylphenol (II) and dimers thereof in accordance with the method set forth above for converting (II) to (I).

The term "lower-alkyl" means alkyl having from 1 to 4 carbon atoms, inclusive, such as methyl, ethyl, propyl, butyl, and isomeric forms thereof.

The term "oligomers" means the dimers, trimers and higher polymers of the compounds of formula (II). The oligomers generally occur in the form of mixtures in which the dimers and trimers predominate. Illustrative of the various dimers and trimers derived from the compounds of formula (II) are:

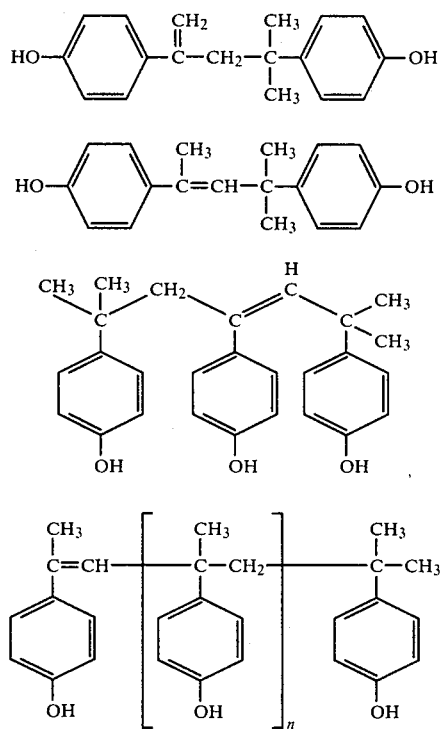

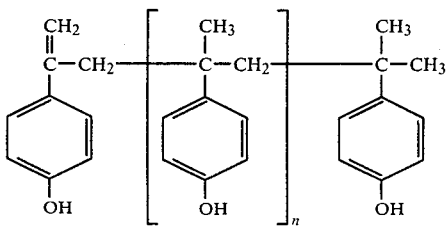

wherein n in both instances is an integer of at least 1. As will be obvious to one skilled in the art many of the above compounds can exist in stereoisomeric form but no attempt has been made to illustrate the individual isomers.

The indanols prepared in accordance with the present invention are useful intermediates in the preparation of various synthetic resins and as antioxidants for natural and synthetic rubbers. The indanols find particular utility in the preparation of polyepoxide resins used in surface coatings, in the preparation of alkyds for paints, and in polyurethanes used in coatings.

DETAILED DESCRIPTION OF THE INVENTION

In carrying out the process of the invention, the starting phenol (II), or any one of the oligomer forms of the starting material, or combinations thereof, is dissolved in one of the organic acids set forth above. Generally speaking, and, with the most preferred organic acids used in accordance with the present invention, the phenol dissolves rapidly and reaction initiates almost immediately upon dissolution at about room temperature (about 20° C.).

In an important and surprising aspect of the present invention, the organic acid is employed in the role of both solvent and catalyst. In point of fact, if the organic acid is used only in catalytic amounts, the advantages which flow from the present process cannot be obtained.

The use of other inert organic solvents in the present process is not specifically excluded. The term "inert organic solvents" means those solvents which do not interact either with the reactants nor with the indanol product, nor interfer in any way with the advantageous features of the present process. Illustrative, but not limiting of solvents which may be used include liquid organic carboxylic acids other than those acids listed above for carrying out the present process, for example, acetic acid, propionic acid, 2-ethylhexanoic acid, and the like; the dipolar aprotic solvents such as dimethylsulfoxide, tetramethylenesulfone, dimethylformamide, dimethylacetamide, N-methylpyrrolidone, hexamethylphosphoramide, acetonitrile, and the like; nitrobenzene, and the like.

Generally speaking, the use of other organic solvents in combination with the organic acid is not necessary, and, in some cases is to be avoided particularly when the organic solvent is not inert and detracts from the present process (see Example 9 below).

The preferred method of carrying out the process in accordance with the present invention is in the absence of any subsidiary solvent.

While all the organic acids set forth above can be used in the practice of the present process, some are more preferred because they dissolve the starting phenols with greater rapidity and give rise to faster reaction rates even at ambient temperatures and below (about 0° C. to about 20° C.) or just slightly above (up to about 50° C.). In this regard, trifluoroacetic acid is a preferred member of the above group.

Others are preferred from the economic standpoint but they require reaction temperatures greater than about 50° C. In this regard, formic acid and chloroacetic acid are then preferred members of the above group.

When trifluoroacetic acid is employed in the present process, no matter what form the phenol is in, monomer or oligomer, or mixtures thereof, it will dissolve rapidly at room temperature (about 20° C.) and the conversion to the indanol proceeds rapidly at that temperature without the need for external heating. When an acid such as formic acid is employed, the dissolution of the phenol compounds can be effected at room temperature but the dimers and particularly trimers require some heating (within the ranges set forth below) in order to dissolve in the acid and for the reaction to proceed at a reasonable rate. Optionally, a trace of any strong acid, for example hydrochloric, sulfuric, etc. can be added to hasten solution of the trimers and higher oligomers in formic acid.

The proportion of organic acid employed in relation to the starting phenol, in contrast to prior art teaching which calls for catalytic amounts of acids, is at least greater than stoichiometric i.e. a molar proportion. That is to say, the acid is always present in a stoichiometric excess (i.e. in excess of the stoichiometric amount). Generally speaking, this means that the acid is used in sufficient excess to form a solution with the phenol. The desired amount of acid to be employed is readily determined by trial and error by one skilled in the art. The maximum amount of acid which can be employed in the present process is limited only by economic and practical considerations. Advantageously, the molar proportions of starting phenol to organic acid can vary from about 1:2 to about 1:60, preferably about 1:3 to about 1:40.

The solution of the starting phenol in the organic acid can be prepared using any convenient method or apparatus known to be suitable by those skilled in the art. Typically, the reactants can be mixed in a closed system such as a reaction kettle, resin flask, glass reaction flask and the like. Alternatively, the reactants can be mixed in an open vessel as no special care is necessary to exclude air or atmospheric moisture. Preferably, the phenol and acid are mixed in a closed but vented system which is equipped for stirring, and, optionally, equipped with a heating mechanism. The order in which the two reactants are added one to the other is not critical. Ordinarily, the phenol reactant is added to the acid and stirring is commenced. The extent of the stirring and duration thereof required to have complete conversion to (I) is easily determined by trial and error methods by one skilled in the art in conjunction with the use of any of the analytical methods discussed below.

Generally speaking, the temperature of the reaction can be the same as the temperature at which the phenol is dissolved in the acid.

Quite unexpectedly, and as noted above, the reaction can be carried out at ambient temperatures (about 20° C.) under some conditions, i.e. the use of the preferred acids. Advantageously, the reaction temperature will fall within a range of from about 0° C. to about 90° C., and preferably from about 15° C. to about 80° C.

The progress of the conversion, i.e. the formation of the indanol compound (I) in the reaction mixture, can be followed by any of the routine analytical procedures employed in the art for such purposes. Illustrative of such procedures are infrared spectral analysis, GLC (gas chromatography), proton nuclear magnetic resonance spectrum analysis, HPLC (high pressure liquid chromatography), and the like. When the formation of the indanol is adjudged complete, for example, on the basis of the complete disappearance of the olefinic function of starting phenol, or by other appropriate assay, the reaction solution is allowed to cool to ambient temperature (if heating was employed) and the indanol recovered from the acid solution by procedures conventional in the art.

For example, the product can be isolated by mixing the acid solution with a non-solvent for the indanol causing the precipitation of the indanol directly as a crystalline product. Typically, water can be used as the non-solvent. The crystalline product is then isolated in a conventional manner, for example by filtration, then washed with fresh water and dried either at atmospheric, or reduced, pressure at an elevated temperature.

Alternatively, the acid solution can be distilled using conventional methods thereby concentrating the solution with respect to the indanol and extracting the product from the residue using organic extractants such as ether, dimethoxyethane, tetrahydrofuran, and the like. The organic solution containing the product can be further purified using conventional extraction methods, i.e. water, sodium carbonate solution, and the like, dried, and then concentrated to yield the purified product.

Alternatively, and, preferably, the product is isolated by recovering the acid (preferably under reduced pressure) and adding a non-solvent for the indanol directly to the residue. While any non-solvent may be used, in order to obtain crystalline products directly, the halogenated hydrocarbon solvents are particularly effective. Illustrative of such solvents are methylene chloride, carbon tetrachloride, chloroform, ethylene dichloride, trichloroethylene, tetrachloroethane, and the like; also halogenated aromatic solvents such as chlorobenzene, ortho- dichlorobenzene, and the like.

The isopropenylphenol starting materials are readily obtainable via methods well known to the art; see patents cited supra and U.S. Pat. No. 4,201,877.

Preferably, the isopropenylphenol starting materials are obtained in the semi-continuous process set forth above.

Phenol is condensed with the ketonic material (III) under acidic conditions to provide the bisphenol compound (IV). Typical of the ketones employed are the aliphatic ketones such as acetone, methyl ethyl ketone, methyl propyl ketone, methyl butyl ketone, and the like.

The bisphenol (IV), with or without purification, is subjected to alkaline pyrolysis or cracking by distillation in the presence of a catalytic amount of an alkali metal hydroxide such as sodium hydroxide, potassium hydroxide, lithium hydroxide and the like, to yield a distillate which is a mixture of phenol and (II).

For a detailed teaching of the methods for carrying out the above steps see U.S. Pat. No. 4,207,265 whose disclosure with respect thereto is incorporated by reference herein.

In the process in accordance with the present invention the phenol must be separated from (II) prior to reaction of the latter with the organic acid. Otherwise, the phenol will react with (II) to reform the bisphenol (IV) as a competing reaction to the indanol formation.

Accordingly, the unreacted phenol is removed from (II), generally speaking, by distillation under reduced pressure. Although the phenol can be separated by other known methods such as extraction and the like, it is preferred to remove it by the distillation technique. Under these conditions the residue remaining after phenol removal is a mixture of predominantly the dimerized form of (II) mixed with a lesser amount of monomer (II) and a very minor amount of starting bisphenol compound, or, under some conditions, a trace amount of oligomer.

The recovered phenol is then employed as part of the starting phenol in a repeat of the above cycle of operations, by combination with additional phenol and ketone (III).

Advantageously, the residue of phenol monomer and dimer with trace amounts of other ingredients noted above can be used directly in the process in accordance with the invention to provide the indanols (I) without requiring any further purification.

The following examples describe the manner and process of making and using the invention and set forth the best mode contemplated by the inventor of carrying out the process of the invention but are not to be construed as limiting.

EXAMPLE 1

A 35 mg. sample of crystalline para-isopropenyl phenol when shaken with 0.42 ml. of pure trifluoroacetic acid in accordance with the present invention, at room temperature (about 20° C.) in a nuclear magnetic resonance (nmr) sample tube, dissolved rapidly to form first a red coloration which subsequently turned to an orange colored solution.

An nmr spectrum was obtained five minutes after the solution was prepared using a Varian A-60 nmr spectrometer. The nmr showed the complete absence of the isopropenyl phenol by the disappearance of the vinylic resonance peaks at $\delta 5.10$ (1) and $\delta 4.75$ (1) and the appearance of three sharp singlets for three methyl protons at high field (i.e. $\delta 1.55$, $\delta 1.24$ and $\delta 1.00$) for the compound [1-(4-hydroxyphenyl)-1,3,3-trimethyl-indanol-6].

EXAMPLE 2

A 2.0 g. sample of a trimer of p-isopropenylphenol [2,6-dimethyl-2,4,6-tris(p-hydroxyphenyl)-heptene-3] was dissolved during stirring in 8.0 g. of trifluoroacetic acid at ambient room temperature (about 20° C.) in a 3-neck reaction flask equipped with a stirrer and reflux condenser in accordance with the present invention. The sample of trimer contained a small proportion (about 10 percent by weight) of the dimer form of the isopropenylphenol namely 4-methyl-2,4-bis(p-hydroxyphenyl)pentene-1. The cis/trans isomer ratio of the trimer was about 85/15 percent by weight.

The stirred solution was constantly monitored by nmr analysis for the disappearance of the starting trimers which occurred in about 10 minutes under the ambient temperature conditions.

The trifluoroacetic acid solution was poured slowly into 250 ml. of cold water during rapid agitation which caused the precipitation of a white solid. The solid was isolated by suction filtration and thoroughly washed with water and dried; wt.=1.95 g; m.p.=163°-176° C.

The solid was triturated with chlorobenzene, collected and dried; wt.=1.88 g. (94% yield); m.p. 183°-186° C. Nmr resonance identified the product as 1-(4-hydroxyphenyl)-1,3,3-trimethyl-indanol-6.

EXAMPLE 3

A 7.00 g. (0.026 mole) sample of 4-methyl-2,4-bis (para hydroxyphenyl)-pentene-1 (i.e. a dimer of para-isoprophenylphenol) was dissolved by stirring with 47.3 g. of trichloroacetic acid at room temperature (about 20° C.) in accordance with the present invention using the apparatus described in Example 2. The reaction solution was stirred overnight (about 15 hours) at ambient temperature (about 20° C.).

The trichloroacetic acid was distilled off under reduced pressure; b.p. (0.1 mm. of Hg)=45°-62° C.; wt. of acid recovered=37.5 g. (79.3% recovery).

The still-pot residue was added to 300 ml. of ice-water followed by extraction with ether. The separated ether layer was washed first with fresh water followed by a wash with sodium bicarbonate solution. The ether solution was dried by storage over anhydrous magnesium sulfate. Evaporation of the ether solution provided a residue of 6.32 g. (90% yield) of 1-(4-hydroxyphenyl)-1,3,3-trimethyl-indanol-6; m.p. 181°-186° C.; structure confirmed by nmr.

EXAMPLE 4

A 70 g. (0.307 mole) sample of 2,2-bis(4-hydroxyphenyl)propane (Bisphenol A) was charged to a 250 ml. flask equipped with a distillation heat along with 0.11 g. of sodium hydroxide. The flask was heated in an oil bath and, under a pressure of 20 mm. of mercury over a period of 40 minutes and at a vapor temperature of 90° to 138° C., there was obtained 68.27 g. of a dissociation product as a distillate.

The distillate obtained above was redistilled under 20 mm. of mercury pressure using an oil bath at 175° C. A distillate of phenol boiling at 85°-88° C. was collected. The pot residue was 43.77 g. of oil. Nmr analysis of the residue disclosed the following components in percent by weight: p-isopropenyl phenol=11%; isopropenyl phenol dimer=78%; isopropenyl phenol trimer and higher oligomers=5%; Bisphenol A=6%.

The hot residue was transferred to a 250 ml. reaction flask equipped according to Example 2 and dissolved by stirring in 137.4 g. of trifluoroacetic acid in accordance with the present invention. The solution was stirred overnight (about 15 hours) at room temperature (about 20° C.). Nmr analysis of the trifluoroacetic acid solution showed the complete absence of olefinic protons.

Evaporation of the reaction solution was carried out in a rotary evaporator under 20 mm. of mercury pressure until the overhead distillation temperature reached 50° C. The sticky black still-pot residue was poured into 500 ml. of water and after shaking the two layers together the aqueous layer was discarded. The organic layer was dissolved in 250 ml. of ether and the ether solution was shaken with dilute sodium bicarbonate solution until no more gas evolution occurred. The ether solution was separated and dried over anhydrous magnesium sulfate. Evaporation of the ether provided a residual oil. The oil was heated with 250 ml of chlorobenzene and the solution allowed to stand overnight. A crystalline product of dried weight of 13.7 g. was collected by suction filtration; m.p. 185°-189° C.; nmr analysis showed the product to be at least 95% 1-(4-hydroxyphenyl)-1,3,3-trimethyl-indanol-6.

A second crop of the crystalline product was obtained after the chlorobenzene filtrate was concentrated to about 120 ml.; wt.=12.7 g.; m.p. 180°-185° C. The overall total product yield from starting Bisphenol A was 66%.

EXAMPLE 5

A 50 mg. sample of 4-methyl-2,4-bis(p-hydroxyphenyl)pentene-1 (a dimer of p-isopropenylphenol) was dissolved in 0.6 ml. of 88 percent formic acid in an nmr tube by heating at 80° C. Nmr analysis was used to monitor the reaction and after 2 hours at the 80° C. level the transformation to 1-(4-hydroxyphenyl)-1,3,3-trimethyl-indanol-6 was complete in accordance with the present invention.

As noted by the time and temperature above, the conversion of the isopropenylphenol dimer to the cyclized indanol product requires more stringent reaction conditions with formic acid than it does with trifluoro- or trichloroacetic acids in the previous examples. In fact, when pure p-isopropenylphenol is dissolved in formic acid at room temperature the product formed is a trimer form of the starting phenol.

Further, in accordance with the present invention, a 4.01 g. sample of the trimer and dimer mixture of p-isopropenylphenol described in Example 2 was dissolved by stirring into 50.1 g. of 88 percent formic acid at 80° C. Because of the inherent insolubility of the trimers, a trace of gaseous hydrogen chloride was bubbled into the formic acid during the dissolution of the trimer-dimer mixture. This enabled the solution to become clear in 15 minutes. The hydrogen chloride is not necessary for the cyclization of the phenols to the indanol but only as a solubilizing aid. The only effect of the absence of the hydrogen chloride is to prolong the dissolution of the phenol mixture. Stirring of the clear solution was continued for 2 hours at 80° C.

The reaction solution was fractionated under reduced pressure to recover the formic acid, b.p. (45 mm. of mercury)=37°-40° C.; wt.=47.5 g. (94.8% recovery). There remained a dark green solid residue. The residue was mixed with 50 ml. of water and the aqueous solution extracted with 3×25 ml. portions of ether. The ether layer was washed (neutralized) with dilute sodium bicarbonate solution and dried by storage over anhydrous magnesium sulfate. The solution was removed under reduced pressure to yield an oily residue. To this residue there was added 43 ml. of chlorobenzene and at 0° C. a crystalline solid precipitated. The solid was collected by suction filtration and dried in a vacuum oven; wt.=3.65 g. (91% yield); m.p.=186°-188° C.; nmr and HPLC analysis confirmed the lone product to be 1-(4-hydroxyphenyl)-1,3,3-trimethyl-indanol-6.

EXAMPLE 6

In accordance with the present invention, a 4.0 g. sample of the trimer and dimer phenol mixture described in Example 2 was dissolved by stirring in 36.7 g. of dichloroacetic acid. In order to speed up the dissolution of the relatively insoluble trimers, the initial solution temperature was about 90° C. to about 100° C. and at this temperature the starting phenols were completely dissolved after 5 minutes. The use of a lower temperature simply results in a longer time period before dissolution of the solids occur. The solution temperature was lowered to 80° C. and stirring continued along with the monitoring of the conversion process by nuclear magnetic resonance analysis on aliquot samples of the solution.

After a 45 minute period the conversion of the phenol mixture to indanol product was complete by nmr measurements. The reaction solution was then vacuum distilled to remove the dichloroacetic acid; b.p. (15 mm of mercury)=70°-88° C., followed by further distillation at lower pressure (0.1 mm.) b.p.=40° C. until no further overhead could be collected. A solid residue remained to which was added 25 ml. of chlorobenzene. This mixture was heated until a solution was obtained. The solution was cooled at 0° C. causing the precipitation of the crystalline product. The solid was collected on a suction filter and dried in a vacuum oven. Thus there was obtained 3.38 g. (84 percent yield) of 1-(4-hydroxyphenyl)-1,3,3-trimethyl-indanol-6; m.p. 183°-186° C.

EXAMPLE 7

In accordance with the present invention, a 40.2 g. sample of a mixture of p-isopropenylphenol (about 12 by weight), dimer of p-isopropenylphenol (about 84 percent), and Bisphenol A (about 4 percent) said mixture being obtained by the pyrolysis reaction of Bisphenol A described in Example 4, was dissolved in 240 g. of molten chloroacetic acid at 80° C. to 85° C. during stirring. The solution was maintained at 80° C. for 2.5 hours causing the color to change from yellow to dark brown. Progress of the reaction was monitored by nuclear magnetic resonance analysis on aliquot samples.

The chloroacetic acid was vacuum distilled from the solution under a pressure of 12 mm. of mercury and a heating bath temperature of 140° to 155° C. The total acid recovery was 234.5 g. (97.7 percent recovery). A solid residue was dissolved by heating in 250 ml. of chlorobenzene. The resulting solution was cooled to 10° C. then stirred overnight. A crystalline solid precipitated which was collected by suction filtration and dried in a vacuum oven. Thus there was obtained 28.5 g (71 percent yield based on BPA as a first crop) of 1-(4-hydroxyphenyl)-1,3,3-trimethyl-indanol-6; m.p. 186°-189° C.

EXAMPLE 8

The following preparation was carried out in accordance with Example 2 of U.S. Pat. No. 3,264,358 except for the work-up procedure. The reference obtained the product as a "brittle resin" by a very high temperature distillation and no indication of yield is given. In the following method a true measure of the yield was required so the product was obtained and isolated as a crystalline material from impurities by a mild extraction procedure.

A 50 ml. round-bottom flask equipped with a stirrer and a condenser was charged with 4.01 g. (0.03 mole) of 4-methyl-2,4-bis(p-hydroxyphenyl)pentene-1 (m.p. 125°-128° C.) and 4.0 g. of concentrated hydrochloric acid. This mixture was heated under reflux in an oil bath at 100°-105° C. for 2 hours.

Efficient stirring was not possible for the whole reaction period because the mixture turned to a thick red paste.

The reaction mixture was cooled and mixed with 25 ml. of water. The aqueous solution which resulted was extracted by 2×25 ml. portions of ether. The combined ether layers were washed with fresh water and then dried by storage over anhydrous magnesium sulfate. The dried ether solution was concentrated in a rotary evaporator to yield 4.35 g. of an oil. HPLC analysis of the oil showed the presence of three components: (1.) the starting pentene-1; (2.) the isomeric pentene-2; and (3.) 1-(4-hydroxyphenyl)-1,3,3-trimethyl-indanol-6.

A 35 ml. portion of chlorobenzene was added and stirred with the oil to form a crystalline solid and the mixture chilled to 0° C. The crystalline precipitate of 1-(4-hydroxyphenyl)-1,3,3-trimethyl-indanol-6 was isolated by suction filtration and oven dried; wt.=1.35 g. (33.7% yield); m.p.=183°–186° C.

EXAMPLE 9

The following experiment serves to illustrate how the presence of isopropyl ether as a particular solvent which is not inert to the process detracts from the advantageous features in accordance with the present invention. At room temperature (about 20° C.) and in the presence of an otherwise requisite amount of trifluoroacetic acid, no desired indanol could be obtained. However, in the absence of the isopropyl ether and at the same temperature, indanol product was obtained.

A 41.11 g. sample of a mixture of p-isopropenylphenol with its dimer and BPA described in Example 7 was dissolved in 100 ml. of isopropyl ether in an Erlenmeyer flask. To the solution was added 50 ml. of trifluoroacetic acid and the solution stirred for 15 minutes. The clear solution was allowed to stand for about 15 hours at room temperature (about 20° C.). A crystalline material which precipitated from the solution was collected by suction filtration; dry wt.=13.5 g.; m.p.=202°–208° C.; nmr analysis showed the material contained the following components (in percent by wt.): (1.) 2,6-dimethyl-2,4,6-tris(p-hydroxyphenyl)heptene-3, cis isomer (59.3%); (2.) trans isomer (24.0%); and (3.) 4-methyl-2,4-bis(p-hydroxyphenyl)pentene-2 (16.7%).

No desired indanol product was obtained. Instead, the effect of the acid treatment in the polar organic solvent upon the starting dimer (pentene-1 isomer) and isopropenylphenol mixture was their conversion to the trimer form of p-isopropenylphenol and formation of the pentene-2 isomer form of the dimer.

The filtrate containing the isopropyl ether, trifluoroacetic acid, and the balance of the starting material (now presumably in the trimer form as the predominant component) was concentrated under reduced pressure in a rotary evaporator to yield a residual oil. In accordance with the present invention there was added to the oil 60 ml. of trifluoroacetic acid and the resulting solution stirred for 1 hour at about 20° C. The solution was concentrated in a rotary evaporator under reduced pressure. A 250 ml. portion of chlorobenzene was added to the remaining oil causing the formation of a crystalline solid. The solid was collected by suction filtration; wt.=8.3 g.; m.p. 185°–188° C.; nmr analysis identified the solid as 1-(4-hydroxyphenyl)-1,3,3-trimethyl-indanol-6.

EXAMPLE 10

The following reactions tabulated in TAble I below as (a) through (g) are not in accordance with the present invention. The general procedure involved dissolving the starting material (IPP=p-isopropenylphenol or dimer of p-isopropenylphenol) in the noted solvent in the percent by weight proportions set forth below and adding the catalyst (at about 2 to 5 percent by weight based on starting material), and stirring the reaction mixture for about 2 hours at room temperature (about 20° C.). In the case of (c) and (d) where a cation was immediately formed (as evidenced by immediate deep color formation) the reaction was run for only a few minutes since no further reaction would proceed; (g) no reaction could be run because the reactants would not form a solution.

TABLE I

| | Starting Material | (% by wt.) | Solv. | Cat. | Product** |
|---|---|---|---|---|---|
| (a) | IPP | (5) | Ethylene dichloride | HCl(g) | Trimers |
| (b) | Dimer | (10) | Diethyl ether | HCl(g) | Trimers |
| (c) | IPP | (15) | CDCl₃ | HCl(g) | 2-chloro-2-(p-hydroxyphenyl)propane |
| (d) | IPP | (4) | H₂SO₄ | H₂SO₄ | — |
| (e) | Dimer* | (6) | CD₃COOH | CD₃COOH | Trimers |
| (f) | Dimer* | (6) | CD₃COOH | CF₃COOH | Trimers |
| (g)*** | IPP | — | Benzene sulfonic acid | — | — |

*Reaction run both at 20° C. and 110° C.
**Products identified by nmr analysis.
***IPP and the sulfonic acid would not form a solution.

The predominant products were the trimers of paraisopropenylphenol, i.e., 2,6-dimethyl-2,4,6-tris(p-hydroxyphenyl)heptene-3, the cis and trans isomers.

Of most significance from the above series is reaction (f) wherein trifluoroacetic acid was employed only in catalytic amount with the solvent being deuterated acetic acid. The only product was the trimer with no evidence of formation of the hydroxyphenyl-indanol compound.

I claim:
1. A method for preparing a hydroxyphenyl-indanol having the formula

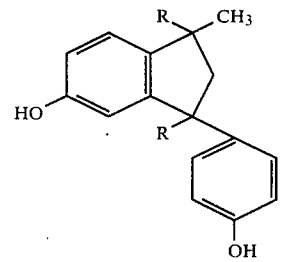

wherein R is lower-alkyl, comprising dissolving a phenol selected from the group consisting of an isopropenylphenol having the formula

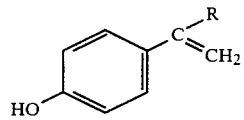

wherein R is defined as above, oligomers thereof, and mixtures of any of said group in any combination and proportion, in a stoichiometric excess of an organic acid selected from the group consisting of trifluoroacetic acid, trichloroacetic acid, difluoroacetic acid, dichloroacetic acid, fluoroacetic acid, chloroacetic acid, formic acid, and mixtures thereof, at a temperature falling within a range of from about 0° C. to about 90° C. to form a solution; and maintaining said solution at a temperature falling within the above said range until the formation of said indanol is substantially complete.

2. The method according to claim 1 wherein said phenol comprises an isopropenylphenol having the formula set forth in claim 1.

3. The method according to claim 1 wherein said phenol comprises a dimer of said isopropenylphenol defined in claim 1.

4. The method according to claim 1 wherein said phenol comprises a trimer of said isopropenylphenol defined in claim 1.

5. The method according to claim 1 wherein said phenol comprises mixtures in any combination and proportion of said isopropenylphenol and oligomers thereof.

6. The method according to claim 1 wherein said organic acid is trifluoroacetic acid.

7. The method according to claim 1 wherein said organic acid is formic acid.

8. the method according to claim 1 carried out in the absence of any subsidiary solvent.

9. A method for preparing [1-(4-hydroxyphenyl)-1,3,3-trimethyl-indanol-6] comprising dissolving a phenol selected from the group consisting of p-isopropenylphenol, oligomers thereof, and mixtures of any of said group in any combination and proportion, in a stoichiometric excess of an organic acid selected from the group consisting of trifluoroacetic acid, trichloroacetic acid, difluoroacetic acid, dichloroacetic acid, fluoroacetic acid, chloroacetic acid, formic acid, and mixtures thereof, at a temperature falling within a range of from about 0° C. to about 90° C. to form a solution; and maintaining said solution at a temperature falling within the above said range until the formation of said indanol is substantially complete.

10. The method according to claim 9 wherein said phenol is a mixture comprising p-isopropenylphenol and a dimer thereof.

11. The method according to claim 8 wherein said organic acid is trifluoroacetic acid.

12. The method according to claim 9 wherein said organic acid is formic acid.

13. A semi-continuous method for the conversion of phenol to a hydroxyphenyl-indanol according to claim 1 which comprises condensing phenol and a ketone of the formula RCOCH$_3$ wherein R is lower alkyl, in the presence of acid to obtain the corresponding bisphenol of formula:

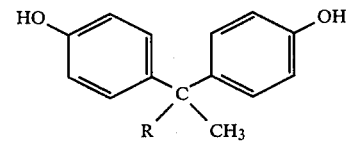

wherein R is defined as above, subjecting said bisphenol to distillation in the presence of a catalytic amount of an alkali metal hydroxide to yield a mixture of phenol and an isopropenylphenol defined in claim 1, recovering the phenol by distilling it from said mixture for reuse as part of the starting material in a subsequent cycle of the above steps, and treating the residue from said distillation, which residue comprises a mixture of said isopropenylphenol and dimers thereof, in accordance with the method set forth in claim 1.

* * * * *

UNITED STATES PATENT OFFICE
CERTIFICATE OF CORRECTION

Patent No. 4,334,106      Dated June 8, 1982

Inventor(s) Shenghong A. Dai

It is certified that error appears in the above-identified patent and that said Letters Patent are hereby corrected as shown below:

Column 2, line 6 "material" should read --materials--;
line 63 "groups" should read --group--.  Column 11,
line 59 "TAble" should read --Table--.  Column 14,
Claim 11, line 6 "claim 8" should read --claim 9--.

Signed and Sealed this

Twelfth Day of October 1982

[SEAL]

Attest:

GERALD J. MOSSINGHOFF

Attesting Officer       Commissioner of Patents and Trademarks